(12) United States Patent
De Jager et al.

(10) Patent No.: US 10,667,888 B2
(45) Date of Patent: Jun. 2, 2020

(54) NOZZLE FOR ORAL IRRIGATOR DEVICE INCLUDING A DYNAMIC NOZZLE ACTUATOR WITH RESPONSIVE MATERIALS

(71) Applicant: KONINKLIJKE PHILIPS N.V., Eindhoven (NL)

(72) Inventors: Marinus Karel Johannes De Jager, Eindhoven (NL); Bart Gottenbos, Budel (NL); Sandra Hoetzl, Eindhoven (NL); Cornelis Petrus Hendriks, Eindhoven (NL); Roland Alexander Van De Molengraaf, Geldrop (NL); Mark Thomas Johnson, Arendonk (BE); Marco Baragona, Delft (NL); Milica Kovacevic Milivojevic, Eindhoven (NL); Valentina Lavezzo, Heeze (NL); Denny Mathew, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 801 days.

(21) Appl. No.: 15/310,461

(22) PCT Filed: May 8, 2015

(86) PCT No.: PCT/IB2015/053366
§ 371 (c)(1),
(2) Date: Nov. 11, 2016

(87) PCT Pub. No.: WO2015/173698
PCT Pub. Date: Nov. 19, 2015

(65) Prior Publication Data
US 2017/0086954 A1    Mar. 30, 2017

Related U.S. Application Data

(60) Provisional application No. 61/992,489, filed on May 13, 2014.

(51) Int. Cl.
*A61C 17/02* (2006.01)
*A61C 17/028* (2006.01)
(Continued)

(52) U.S. Cl.
CPC ........ *A61C 17/0202* (2013.01); *A61C 17/028* (2013.01); *A61H 13/005* (2013.01);
(Continued)

(58) Field of Classification Search
CPC .............. A61C 2201/007; A61C 17/02; A61C 17/0202; A61C 17/028; A61C 17/0211;
(Continued)

(56) References Cited

U.S. PATENT DOCUMENTS 3,739,983 A    6/1973    Joussen
3,958,249 A *  5/1976    DeMaine ................... B41J 2/02
                                                          347/75
(Continued)

FOREIGN PATENT DOCUMENTS

DE    3526579 A1    7/1986
WO    2008106298 A1    9/2008
WO    2013061251 A1    5/2013

*Primary Examiner* — Bradley H Philips
*Assistant Examiner* — Vincent D Hoang

(57) ABSTRACT

A nozzle (12) for an oral irrigator device (10) having a guidance tip (34) with an orifice at one end, and a dynamic nozzle actuator (64) positioned within said guidance tip. The orifice (36) is configured to expel a fluid as one of a jet, a spray, or any combination thereof. The dynamic nozzle actuator (64) comprises at least one responsive material adapted for being energized and configured to implement at least one dynamic actuation of an effective channel (62) for dynamically influencing at least one of (i) a direction of fluid expelled from the orifice (36), (ii) an angle of fluid expelled
(Continued)

from the orifice (36), (iii) a cross-sectional width of fluid expelled from the orifice (36), and (iv) any combination thereof.

11 Claims, 14 Drawing Sheets

(51) Int. Cl.
*A61H 13/00* (2006.01)
*A61M 3/02* (2006.01)
(52) U.S. Cl.
CPC ........ *A61M 3/0275* (2013.01); *A61M 3/0279* (2013.01); *A61C 2201/007* (2013.01); *A61M 2205/0266* (2013.01); *A61M 2205/0283* (2013.01); *A61M 2205/0294* (2013.01)
(58) Field of Classification Search
CPC .. A61M 2205/0266; A61M 2205/0272; A61M 2205/0283; A61M 2205/0294; A61M 3/0275; A61M 3/0279; B05C 5/0262

USPC .............. 601/162, 163; 239/546, 102.2, 602, 239/DIG. 19
See application file for complete search history.

(56) References Cited

U.S. PATENT DOCUMENTS

| | | | |
|---|---|---|---|
| 7,185,833 B2* | 3/2007 | Geskin | B05B 1/02 239/533.1 |
| 2008/0311540 A1* | 12/2008 | Gottenbos | A61C 17/02 433/86 |
| 2009/0017423 A1* | 1/2009 | Gottenbos | A61C 17/028 433/216 |
| 2010/0331769 A1 | 12/2010 | Nisato et al. | |
| 2012/0276497 A1 | 11/2012 | Gharib et al. | |
| 2013/0196084 A1 | 8/2013 | Decher et al. | |
| 2014/0099597 A1* | 4/2014 | Bergheim | A61C 1/07 433/80 |

* cited by examiner

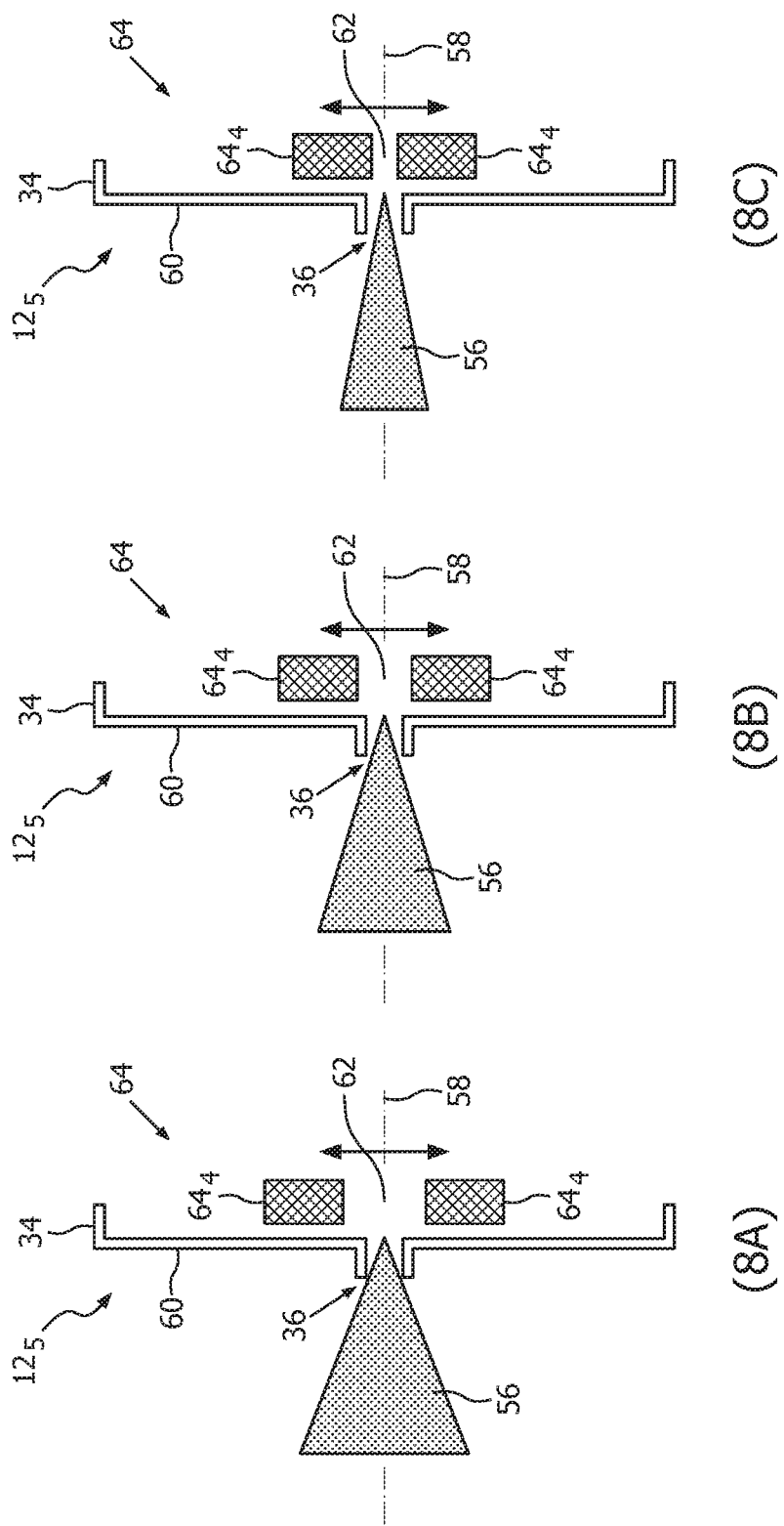

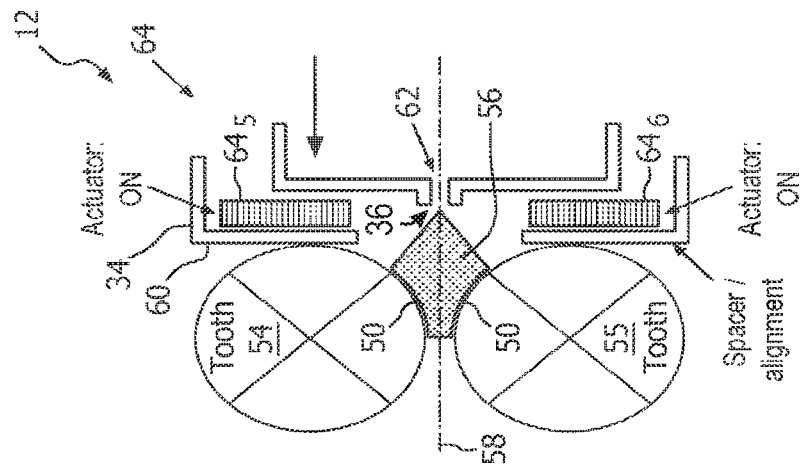
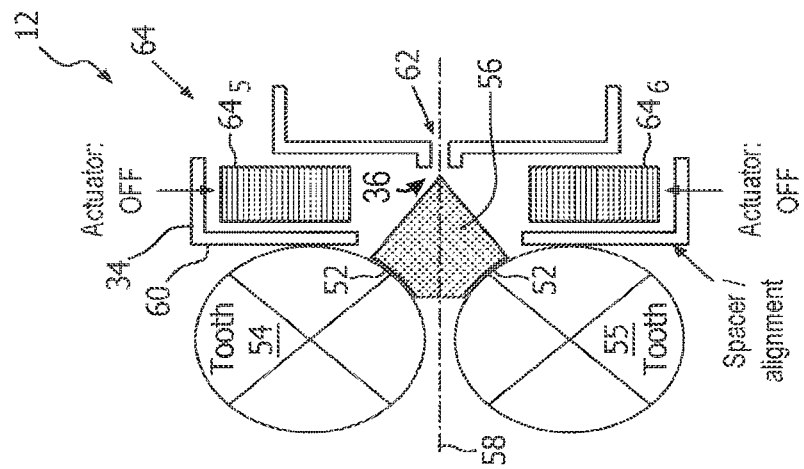
FIG. 9

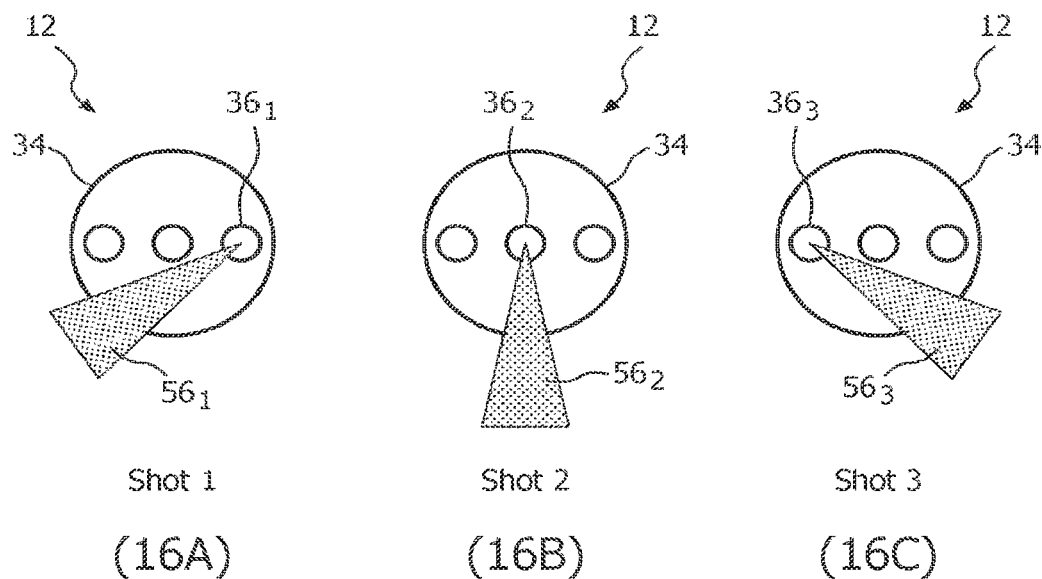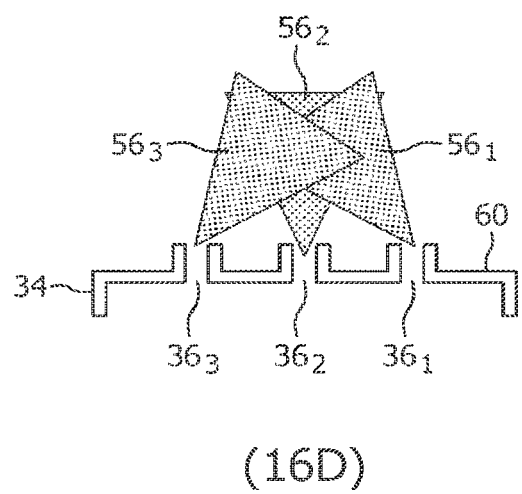
FIG. 16

NOZZLE FOR ORAL IRRIGATOR DEVICE INCLUDING A DYNAMIC NOZZLE ACTUATOR WITH RESPONSIVE MATERIALS

CROSS-REFERENCE TO PRIOR APPLICATIONS

This application is the U.S. National Phase application under 35 U.S.C. § 371 of International Application No. PCT/IB2015/053366, filed on May 8, 2016, which claims the benefit of U.S. Provisional Patent Application No. 61/992,489, filed on May 13, 2014. These applications are hereby incorporated by reference herein.

The present embodiments relate generally to flossing devices and methods in the field of oral healthcare and, more particularly, to oral irrigator devices and methods including a dynamic nozzle actuator with responsive materials.

One example of a device for use in cleaning between teeth is a Sonicare AirFloss device available from Philips Oral Healthcare, Inc. The oral care device is based upon a microburst technology that delivers a quick burst of air and liquid to effectively yet gently clean between teeth. The oral care device is designed to remove dental plaque biofilms from the interdental areas between teeth to improve gingival health through the use of the high-velocity droplet spray. It aims is to be at least as effective as ordinary string flossing and conventional oral irrigators/water jets, while much easier and more comfortable to use. In practice, however, the efficacy may be limited since the area reached effectively is limited by the nozzle design, with a fairly narrow and focused spray on the so-called approximal area below the contact points of neighbouring teeth towards the gingival tissue. As a consequence, the more accessible and visible interproximal surfaces may not be cleaned as thoroughly. For convenience, as used herein, interdental plaque comprises approximal plaque and interproximal plaque.

Accordingly, an improved method and apparatus for overcoming the problems in the art is desired. In particular, it would be desirable to increase an effective interdental area covered by the nozzle.

In accordance with the embodiments of the present disclosure, oral irrigator device nozzles and methods are configured to advantageously increase an effective interdental area covered by a nozzle. The increased effective interdental area is achieved using dynamic actuation of an orifice in either a nozzle head or only a nozzle outlet. Dynamic actuation further advantageously enables a wider spray angle and/or multiple spray directions to be achieved. Dynamic actuations are implemented using responsive materials to allow for compact and effective solutions that can be embedded within a limited volume of a given nozzle.

In accordance with one aspect of the present disclosure, a nozzle for an oral irrigator device has a guidance tip located at one end that includes an orifice configured to expel a fluid as one of a jet, a spray, or any combination thereof; and a dynamic nozzle actuator positioned within the guidance tip, wherein said dynamic nozzle actuator comprises at least one responsive material adapted for being energized to implement at least one dynamic actuation of an effective channel for dynamically influencing at least one of (i) a direction of fluid expelled from the orifice, (ii) an angle of fluid expelled from the orifice, (iii) a cross-sectional width of fluid expelled from the orifice, and (iv) any combination thereof.

In one embodiment, the dynamic nozzle actuator imparts a motion to the effective channel by translating the effective channel between at least one of a first and second position.

In a further aspect, the dynamic nozzle actuator translates the effective channel between positions in an iterative manner for consecutive bursts of expelled fluid.

In a still further aspect, the orifice comprises the effective channel and the responsive material further comprises a spring-like actuator configured to tilt an outer surface of the guidance tip in an oscillating manner.

Advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 10:
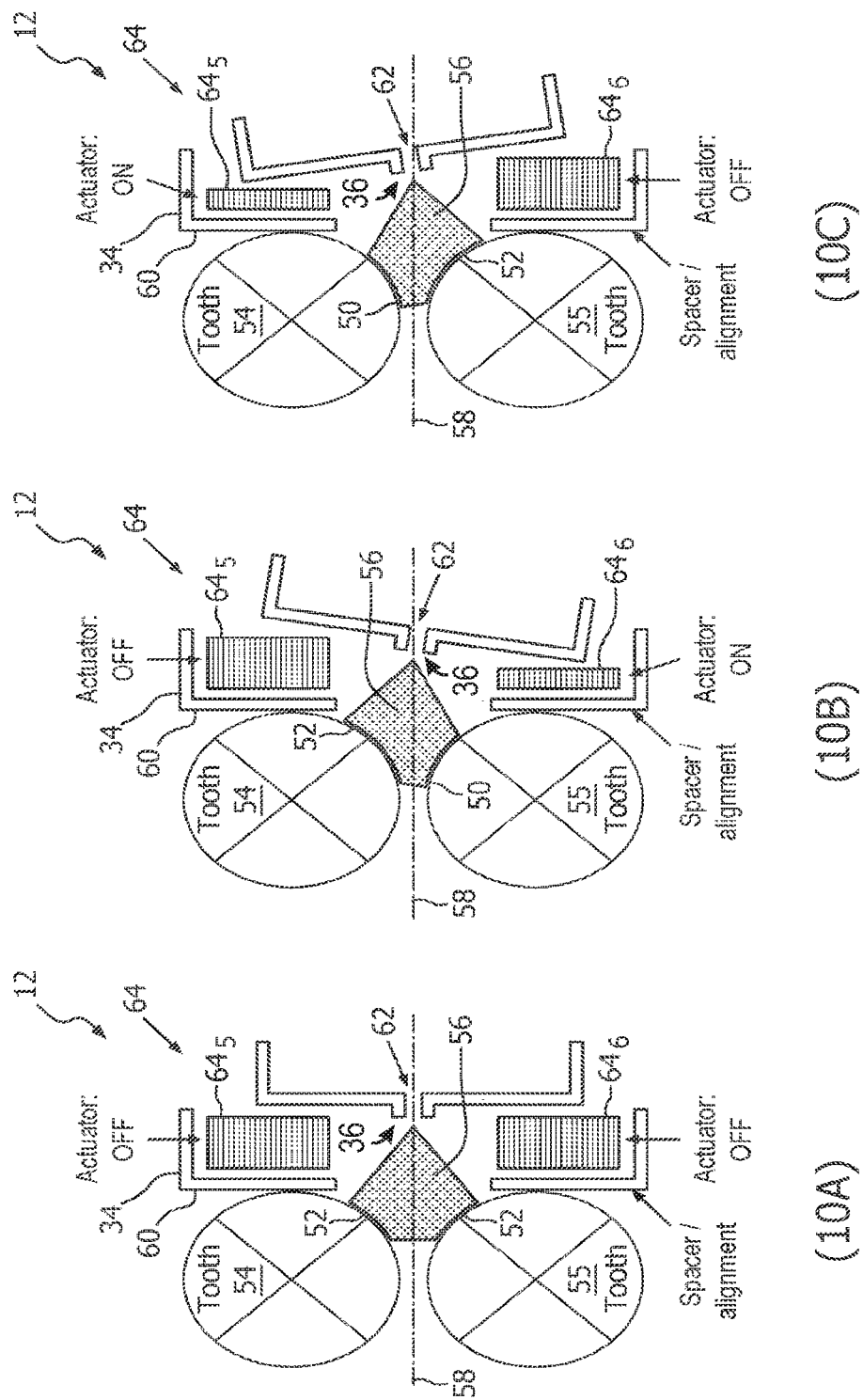
Figure 11:
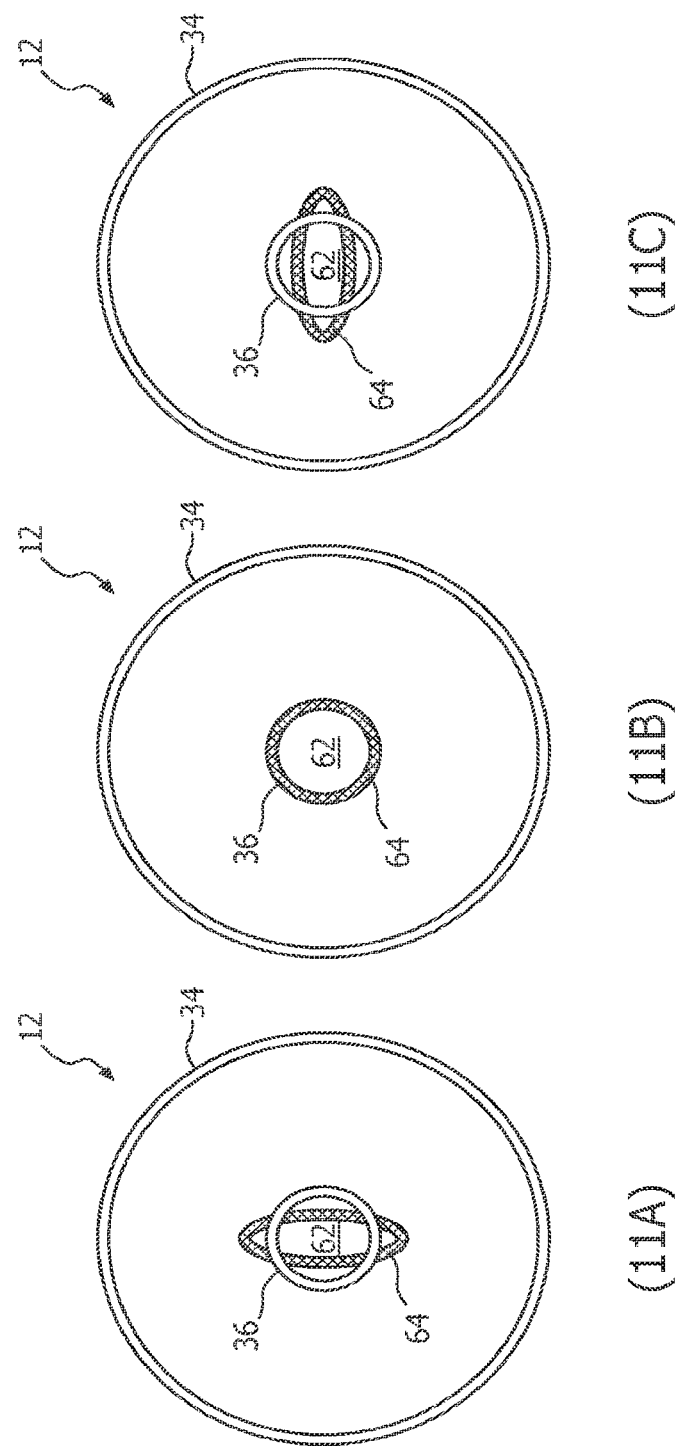
Figure 12:
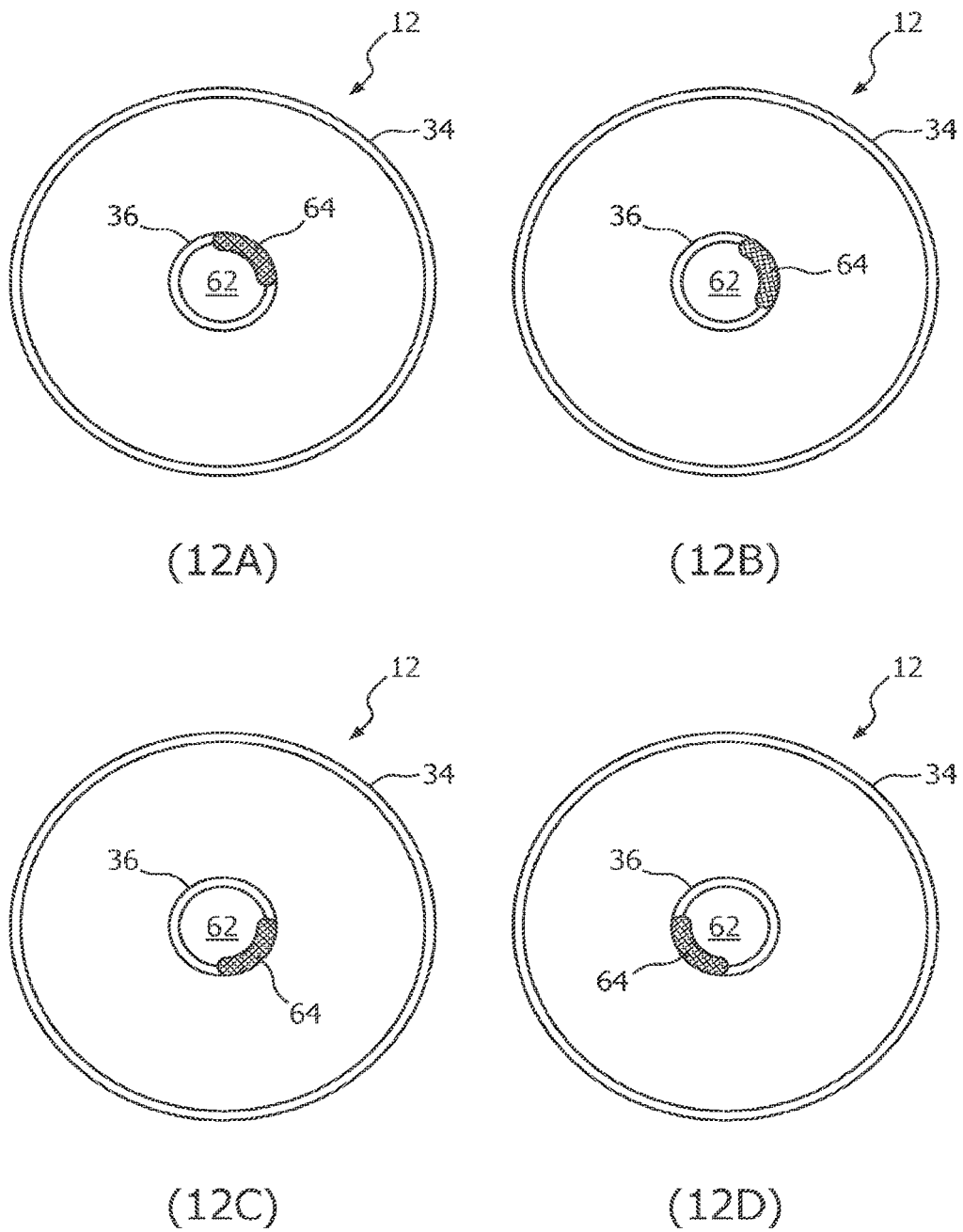
Figure 13:
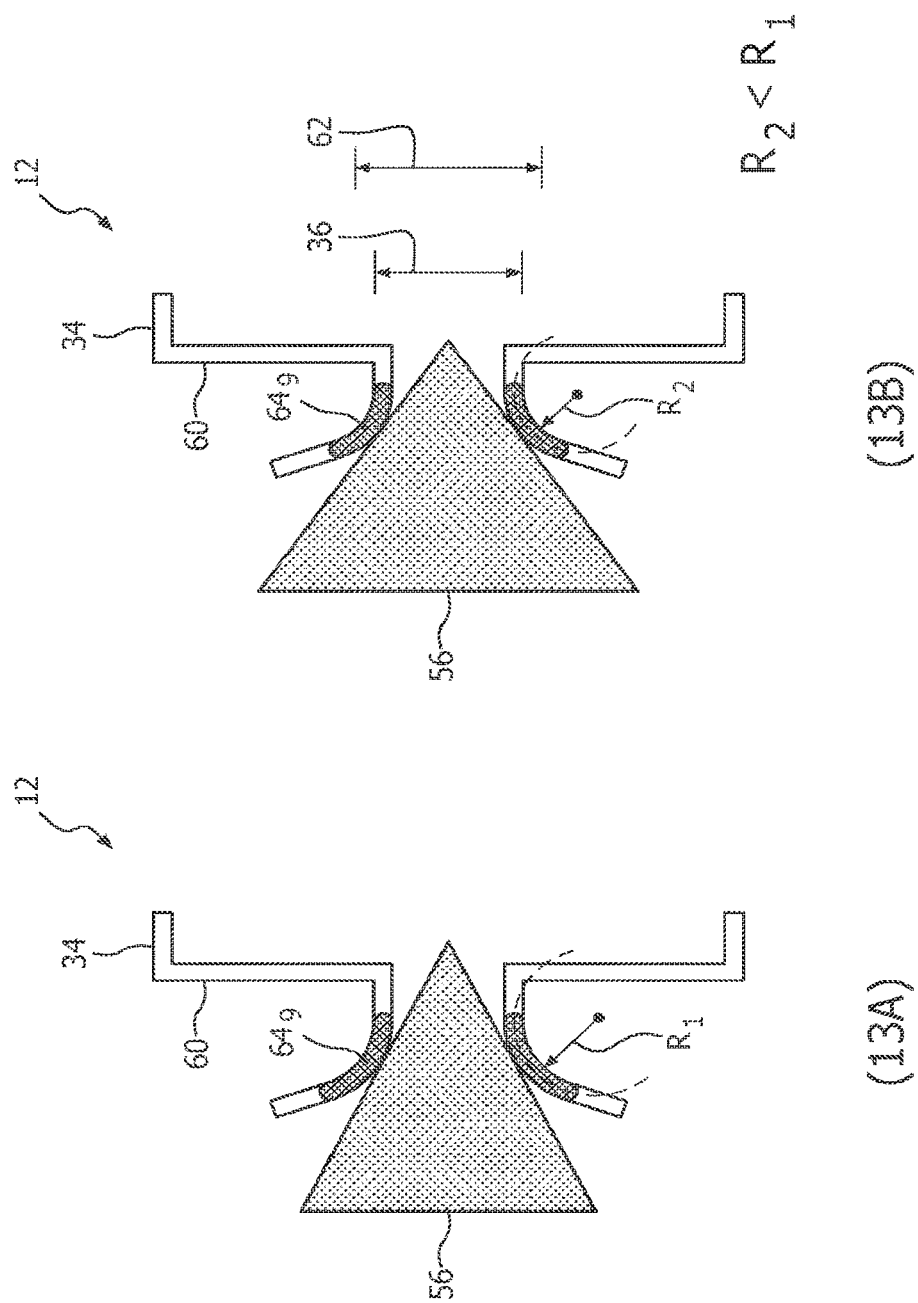
Figure 14:
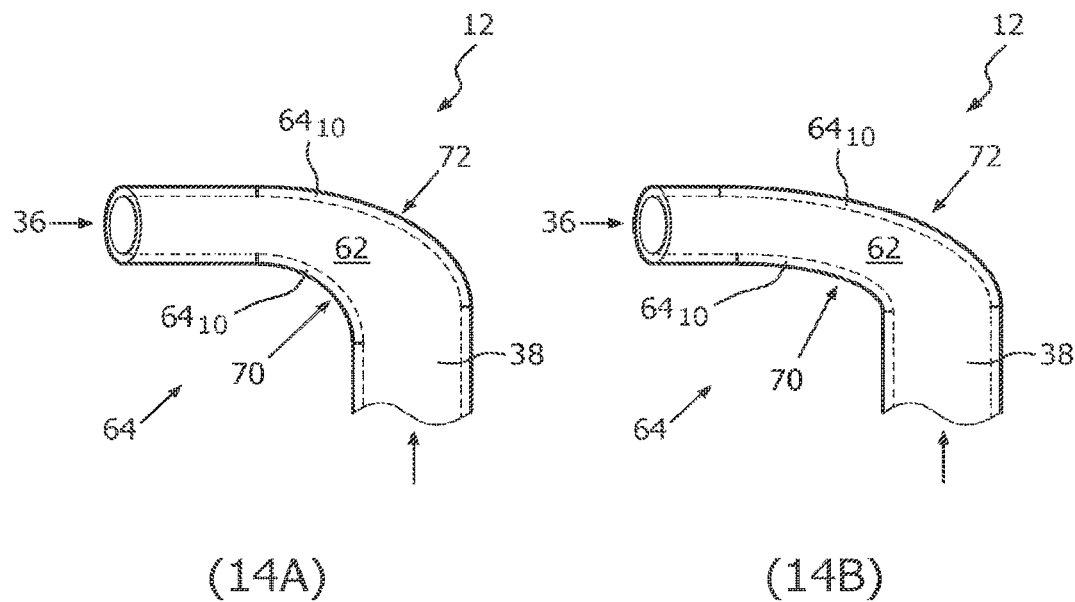
Figure 15:
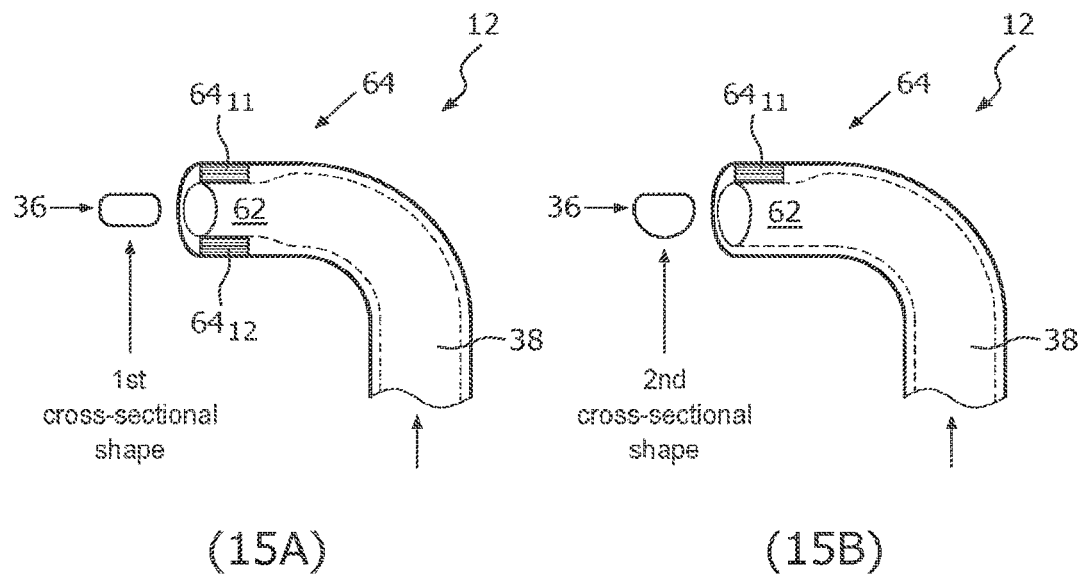
Figure 17:
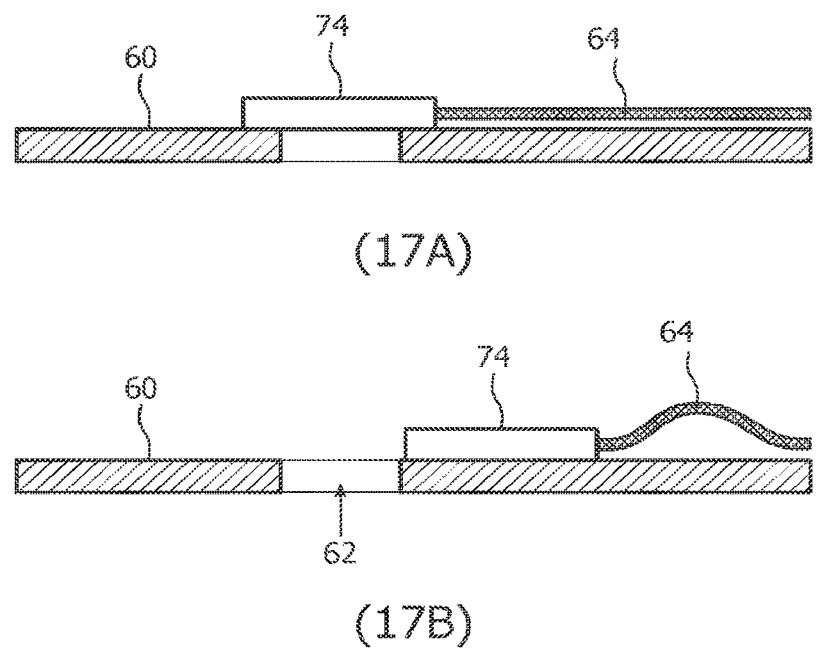

FIG. 8 (8A, 8B, 8C) is a sectional view of a nozzle design of an oral irrigator device including a dynamic nozzle actuator 64 for translating an effective channel 62 between at least two different sizes in a symmetrically narrowing or enlarging of the effective channel 62 according to an embodiment of the present disclosure;

FIG. 9 (9A, 9 B) is a sectional view of a nozzle design of an oral irrigator device including a dynamic nozzle actuator 64 for imparting a motion to an effective channel 62 between at least a first axial position and a second axial position, different from the first axial position, according to an embodiment of the present disclosure;

FIG. 10 (10A, 10B, 10C) is a sectional view of a nozzle design of an oral irrigator device including a dynamic nozzle actuator 64 for imparting a motion to an effective channel 62 by rotating the effective channel 62 between at least a first radial position and a second radial position according to an embodiment of the present disclosure;

FIG. 11 (11A, 11B, 11C) is a top view of a nozzle design of an oral irrigator device including a dynamic nozzle actuator 64 for imparting a motion to an effective channel 62 by resizing a cross-sectional shape of the effective channel 62 between at least a first shape and a second shape according to an embodiment of the present disclosure;

FIG. 12 (12A, 12B, 12C, 12D) is a top view of a nozzle design of an oral irrigator device including a dynamic nozzle actuator 64 for dynamically altering one or more segments of a cross-sectional shape of an effective channel 62 between at least two different altered cross-sectional shapes according to an embodiment of the present disclosure;

FIG. 13 (13A, 13B) is a sectional view of a nozzle design of an oral irrigator device including a dynamic nozzle actuator 64 for dynamically altering one or more segments of an effective channel 62 to have a radius of curvature that is varied between at least two different radii according to another embodiment of the present disclosure;

FIG. 14 (14A, 14B) is a sectional view of a nozzle design of an oral irrigator device including a dynamic nozzle actuator 64 for dynamically altering one or more segments of a cross-sectional shape of an effective channel between at least two different altered cross-sectional shapes according to another embodiment of the present disclosure;

FIG. 15 (15A, 15B) is a sectional view of a nozzle design of an oral irrigator device including a dynamic nozzle actuator 64 for dynamically altering one or more actuator segments of a cross-sectional shape of an effective channel 62 between at least two different altered cross-sectional shapes according to another embodiment of the present disclosure;

FIG. 16 (16A, 16B, 16C, 16D) is a top view and a sectional view of a nozzle design of an oral irrigator device including a plurality of orifices and a dynamic nozzle actuator 64 for dynamically influencing fluid expelled from the plurality of orifices and for multiplexing the fluid expelled from among the plurality of orifices according to an embodiment of the present disclosure; and FIG. 17 is a sectional view of a valve for use with the plurality of orifices of the multichannel nozzle of FIG. 16 according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Figure 1:
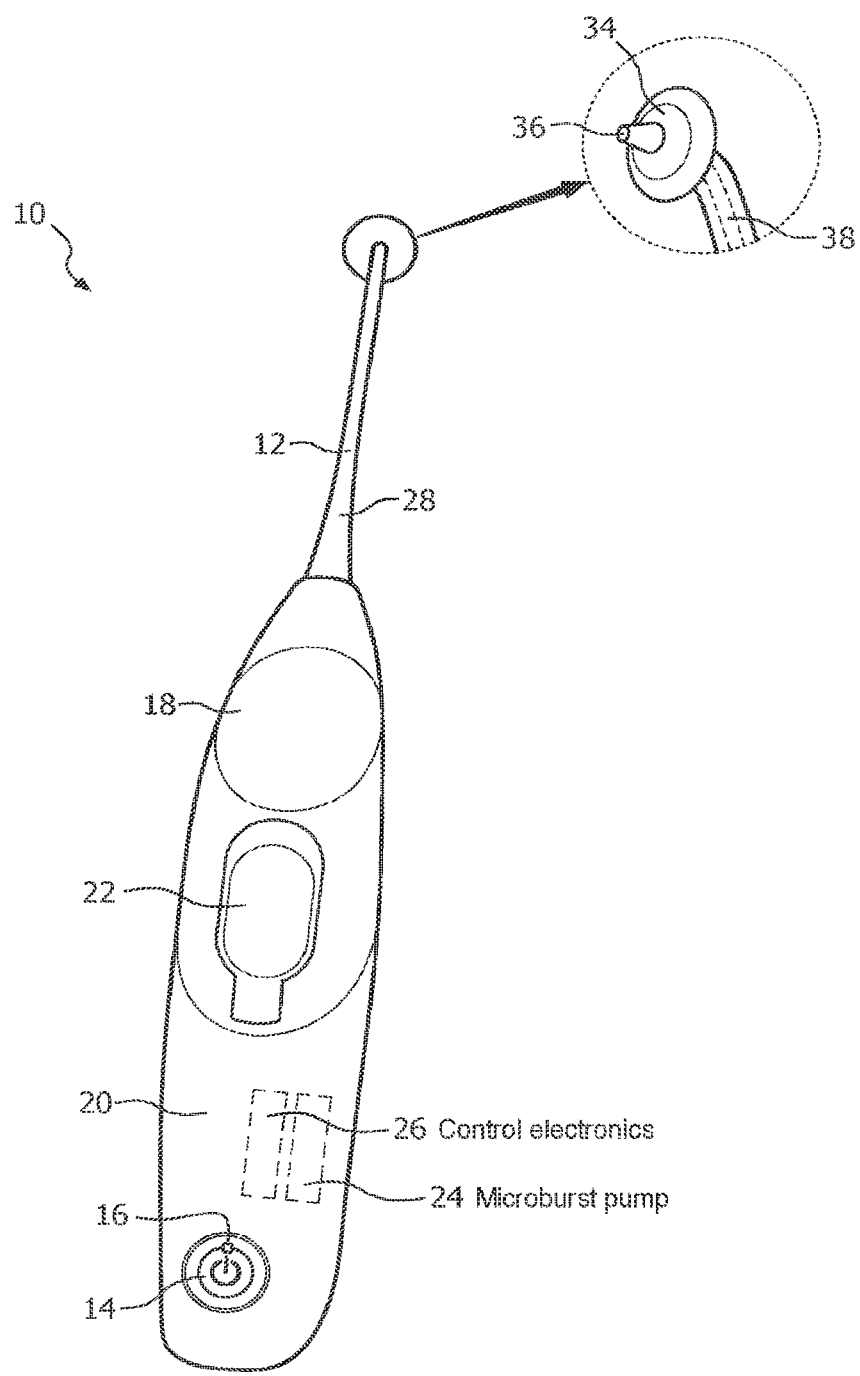
FIG. 1 is a perspective view of an oral irrigator device including a nozzle with a guidance tip and dynamic nozzle actuator according to an embodiment of the present disclosure.

With reference now to FIG. 1, a perspective view of an oral irrigator device 10 including a nozzle 12 according to an embodiment of the present disclosure is shown. The oral irrigator device 10 includes a power ON/OFF button 14, a charge indicator 16, an activation button 18, an ergonomic handle 20, a fluid reservoir 22, a microburst pump 24, and control electronics 26. The nozzle 12 includes an elongated body 28 having a proximal end, and a distal end. The distal end includes a guidance tip 34 with an orifice 36, wherein the orifice 36 is configured to exhaust a fluid as one of a jet, a spray, or any combination thereof, to be discussed further herein below. The proximal end of the elongated body 28 is configured for being coupled to a distal end of the handle 20 of the oral irrigator device 10. Responsive to coupling of the proximal end of the elongated body 28 to the distal end of the handle 20, an appropriate connection between the reservoir 22 and the orifice 36, via channel 38, are made for a given implementation. In the embodiments of the present disclosure, the control electronics 26 comprise any suitable controller, microcontroller, processor, power source and/or other electronics to provide power and control signals for implementing the various dynamic actuation functions, or any combination thereof, as discussed further herein.

In one embodiment, the activation button 18 of the oral irrigator device 10 is operable between (a)(i) an OFF state and (a)(ii) at least one activation ON state. The at least one activation ON state can comprise one or more states for causing (b)(i) the pump 24 to be operable to pump the fluid from the reservoir 22 to the channel 38 and the orifice 36 exhausts the fluid as one of a jet, a spray, or any combination thereof, and (b)(ii) the control electronics 26 to be operable to energize the at least one responsive material of the dynamic nozzle actuator to implement at least one dynamic actuation of an effective channel for dynamically influencing at least one of (i) a direction of fluid expelled from the orifice, (ii) an angle of fluid expelled from the orifice, (iii) a cross-sectional width of fluid expelled from the orifice, and (iv) any combination thereof, as discussed further herein.

Figure 2:
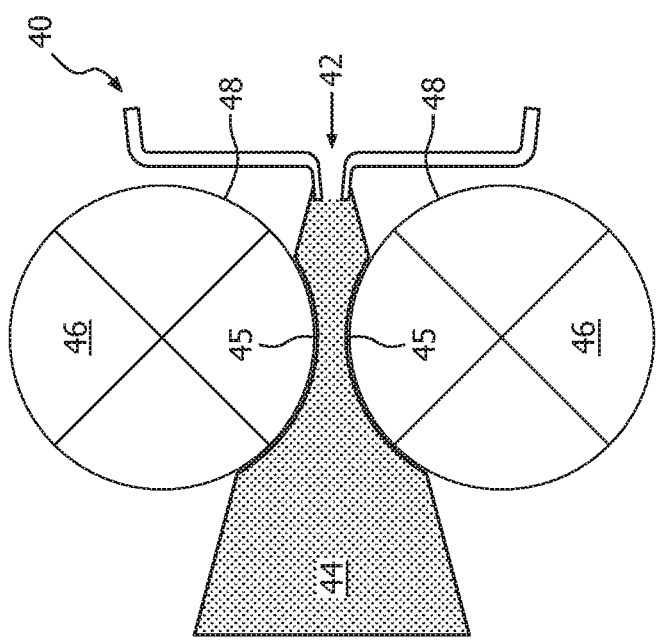
FIG. 2 is a schematic view of an existing nozzle design of a known oral irrigator device having an interproximal reach that targets approximal plaque only.

Turning now to FIG. 2, there is shown a schematic view of an existing nozzle 40 of a known oral irrigator device of the prior art having an interproximal reach that targets approximal plaque only. The nozzle 40 comprises a static, non-dynamic nozzle with an orifice 42 that is stationary with respect to the nozzle. In addition, an efficacy of the nozzle 40 is limited since the area reached effectively is limited by the nozzle design, with a fairly narrow and focused spray 44 on the so-called approximal area, generally indicated by reference numeral 45, below the contact points of neighbouring teeth 46 towards the gingival tissue. As a consequence, the more accessible and visible interproximal surfaces, indicated by reference numeral 48, are not as affected.

Figure 3:
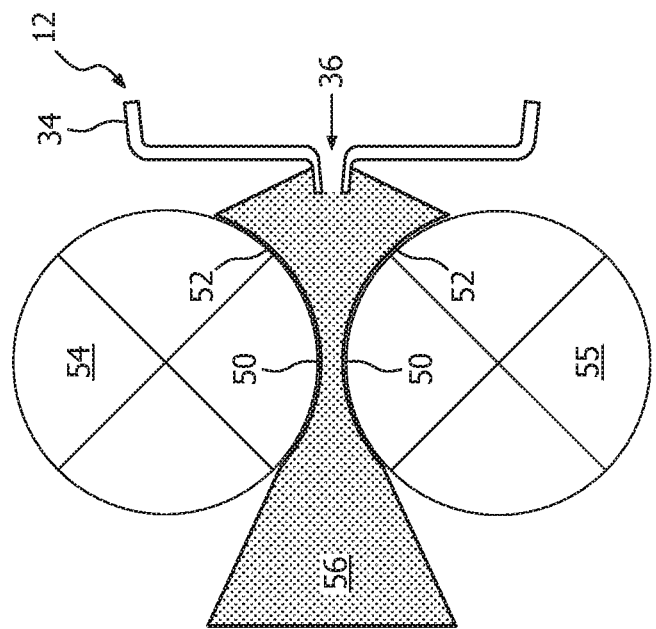
FIG. 3 is a schematic view of a nozzle design of an oral irrigator device having an interproximal reach that targets both approximal and interproximal plaque according to an embodiment of the present disclosure.

With reference now to FIG. 3, there is shown a schematic view of a guidance tip 34 of nozzle 12 of an oral irrigator device 10 of the present invention having an interproximal reach that targets both approximal plaque and interproximal surface plaque, generally indicated by reference numerals 50 and 52, respectively, of neighbouring teeth 54 and 55, according to an embodiment of the present disclosure. Guidance tip 34 of nozzle 12 includes an orifice 36 configured to expel a fluid as one of a jet, a spray, or any combination thereof. To increase efficacy of the oral irrigator device, its effective reach is increased from the approximal areas targeted with an existing nozzle design, as shown in FIG. 2, to extend beyond this area and include a larger fraction of the interproximal plaque areas, as shown in FIG. 3, e.g., by using a wider spray.

Figure 4:
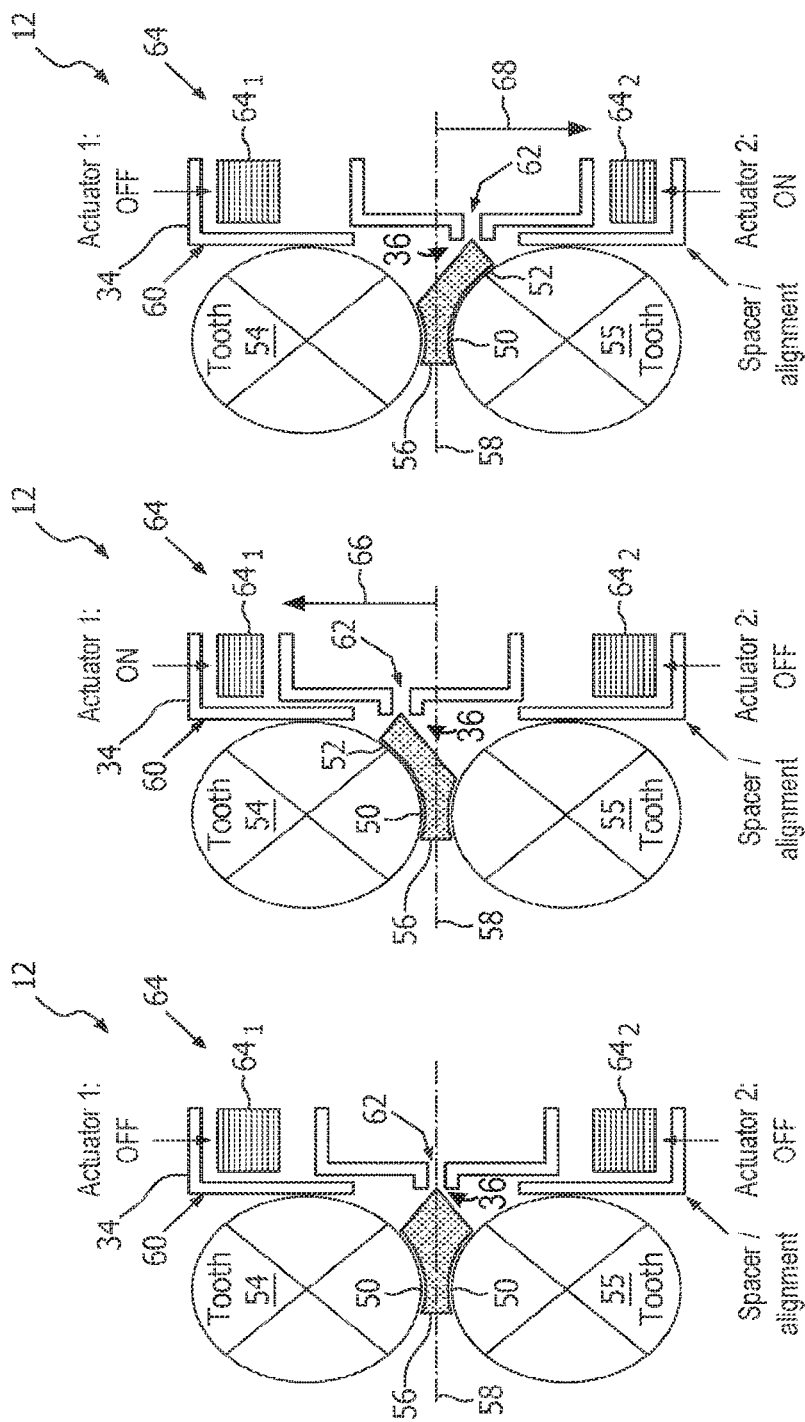
FIG. 4 (4A, 4B, 4C) is a sectional view of a nozzle design of an oral irrigator device including a dynamic nozzle actuator for imparting a motion to an effective channel by translating the effective channel according to an embodiment of the present disclosure.

With reference now to FIG. 4 (4A, 4B, 4C), there is shown a sectional view of a nozzle 12 of an oral irrigator device 10 including a dynamic nozzle actuator for imparting a motion to an effective channel 62 by translating the effective channel 62 according to an embodiment of the present disclosure. As indicated herein above, the oral irrigator device nozzles and methods according to the embodiments of the present disclosure are configured to advantageously increase an effective interdental area covered by a nozzle. The increased effective interdental area is achieved using dynamic actuation of an orifice in either a nozzle head or only a nozzle outlet. Dynamic actuation further advantageously enables a wider spray angle and/or multiple spray directions to be achieved. Dynamic actuations are implemented using responsive materials to allow for compact and effective solutions that can be embedded within a limited volume of a given nozzle.

As shown in FIG. 4, the orifice 36 includes a principal axis 58 of the guidance tip 34. In addition, an effective channel 62 has a home position centered on the principal axis 58 of the orifice 36 (e.g., FIG. 4A). As will be discussed herein, at least one dynamic actuation of the effective channel 62 comprises a motion imparted to the effective channel selected from the group consisting of translation, rotation, resizing, and any combination thereof.

As shown in FIG. 4, at least one dynamic actuation of the effective channel 62 comprises a translation motion imparted to the effective channel 62. The nozzle 12 includes a dynamic nozzle actuator 64 (indicated by reference numerals $64_1$ and $64_2$) that imparts a motion to the effective channel 62 by translating the effective channel 62 between at least a first lateral position (e.g., FIG. 4B) and a second lateral position (e.g., FIG. 4C), wherein the first and second lateral positions of the effective channel are different lateral positions perpendicular to the principal axis 58 of the orifice 36. Note that there are at least three different lateral positions of the effective channel 62, such as shown in FIGS. 4A, 4B, and 4C.

In one embodiment, responsive to a control signal from control electronics 26 (FIG. 1), the dynamic nozzle actuator 64 translates the effective channel 62 in an iterative manner, i.e., between different lateral positions, for consecutive bursts of expelled fluid. The different lateral positions may correspond to the positions illustrated in FIGS. 4A, 4B and 4C, as well as any other intermediate lateral positions. In one position as shown in FIG. 4A, the effective channel 62 has a home position located with respect to the principal axis 58 that corresponds with being centered on the principal axis 58 of the orifice 36. In this position, the guidance tip 34 of nozzle 12 has an interproximal reach that targets approximal plaque, generally indicated by reference numeral 50, of neighbouring teeth 54 and 55. In another position as shown in FIG. 4B, the effective channel 62 has a position located with respect to the principal axis 58 that corresponds with being laterally displaced in a first lateral direction 66 from the principal axis 58 of the orifice 36. In this position, the guidance tip 34 of nozzle 12 has an interproximal reach that targets approximal plaque and interproximal surface plaque, generally indicated by reference numerals 50 and 52, of the first tooth 54. In yet another position as shown in FIG. 4C, the effective channel 62 has a position located with respect to the principal axis 58 that corresponds with being laterally displaced in a second lateral direction 68 from the principal axis 58 of the orifice 36. In this position, the guidance tip 34 of nozzle 12 has an interproximal reach that targets approximal plaque and interproximal surface plaque, generally indicated by reference numerals 50 and 52, of the second tooth 55, neighbouring the first tooth 54. Accordingly, the lateral movement of the effective channel 62 of the nozzle tip from which the spray exits advantageously increases coverage of the spray.

With reference still to FIG. 4, the dynamic nozzle actuator 64 comprises a first actuator $64_1$ and a second actuator $64_2$. In one embodiment, the first and second actuators comprise at least one responsive material. The at least one responsive material comprises one or more of (i) an electro-active polymer (EAP), (ii) a shape memory alloy (SMA), (iii) a bimetal, and (iv) a piezo (PZT) material. A brief discussion of responsive materials will now be presented herein below.

Responsive materials for use with the embodiments of the present disclosure are selected according to the requirements of a particular oral irrigator implementation. Responsive materials can comprise any suitable dry responsive material or materials characterized by an indication of mechanical characteristics with a fast and reversible response, for example, as shown in Table 1. One or more types of responsive material may be included in a single implementation of a given oral irrigator device, according to the requirements of the oral irrigator device.

TABLE 1

Mechanical Characteristics of Dry Responsive Materials

| Material | Actuation Stress (MPa) | Strain (%) | Switch-rate | Actuation (field, temperature, wavelength) |
| --- | --- | --- | --- | --- |
| Dielectric elastomers | <7 | 5-300% | Hz-KHz | 50-150 V/µm |
| PVDF Relaxor polymers | <50 | 1-8% | Hz-KHz | 50-120 V/µm |
| Shape Memory Alloys | 100-1000 | 1-8% | 0.01 Hz-Hz | −20/+150° C. |
| Piezoceramic actuators | <100 | 0.1% | Hz-KHz | 3 V/µm |
| Liquid crystal polymer networks (light sensitive) | 0.1 | 1% | Hz-KHz | light 350-450 nm |

With reference again to FIGS. 4 and 1, the control electronics 26 is operable to energize the dynamic nozzle actuator 64 in a prescribed manner to facilitate and/or implement at least one dynamic actuation of the effective channel, as discussed herein. For example, in one embodiment, the control electronics 26 of FIG. 1 are configured to control the dynamic nozzle actuator 64 (i) with both actuators $64_1$ and $64_2$ OFF as shown in FIG. 4A, (ii) with the first actuator $64_1$ ON and the second actuator $64_2$ OFF as shown in FIG. 4B, (iii) with the first actuator $64_1$ OFF and the second actuator $64_2$ ON as shown in FIG. 4C, and (iv) any other suitable control of the dynamic nozzle actuator activation or activations for a given oral irrigator implementation. In one embodiment, an energizing of an actuator to an ON state results in a contraction of the responsive material and the energizing of the actuator from the ON state to an OFF state results in an expansion of the responsive material to its non-energized condition or state. In another embodiment, the opposite may apply, wherein an ON state results in expansion of the responsive material and the OFF state results in a contraction of the responsive material.

In addition, the energizing, via the control electronics 26, of the dynamic nozzle actuator 64 to implement the at least one dynamic actuation of the effective channel 62 which dynamically influences at least one of (i) a direction of fluid expelled from the orifice 36, (ii) an angle of fluid expelled from the orifice 36, (iii) a cross-sectional width of fluid expelled from the orifice 36, and (iv) any combination thereof. In other words, slight vertical or lateral movement of the effective channel of the nozzle outlet/head to direct the spray to cover a wider area is realized by using actuators comprised of responsive materials that can deform sufficiently under the influence of an electrical or optical signal, and further to coincide with a timing of either a single shot or multiple shots of microburst fluid.

Figure 5:
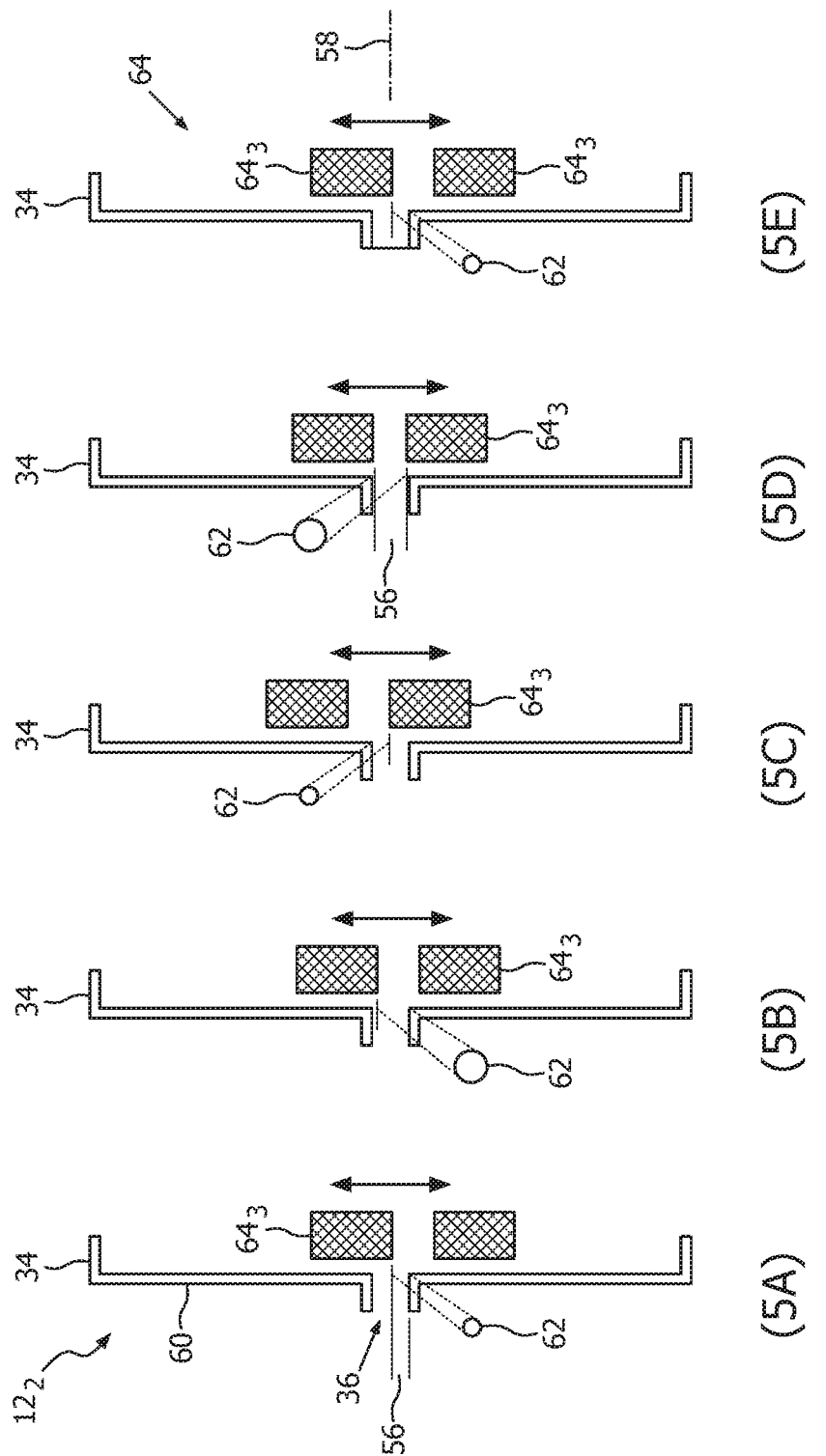
FIG. 5 (5A, 5B, 5C, 5D, 5E) is a sectional view of a nozzle design of an oral irrigator device including a dynamic nozzle actuator for imparting a motion to one or more actuators for partially blocking an orifice 36 according to an embodiment of the present disclosure.

With reference now to FIG. 5 (5A, 5B, 5C, 5D, 5E), there is shown a sectional view of a guidance tip 34 of a nozzle 12 of the present invention including a dynamic nozzle actuator 64 for imparting a motion to one or more actuators $64_3$ for partially blocking an orifice 36 according to an embodiment of the present disclosure. In particular, the dynamic nozzle actuator 64 imparts a motion to the effective channel 62 by translating the effective channel between at least two different sizes in an asymmetrically narrowing or enlarging of the effective channel. In FIG. 5, the at least one dynamic actuation of the effective channel 62 comprises a translation and resizing motion imparted to the effective channel 62. The nozzle 12 includes a dynamic nozzle actuator 64 that imparts a motion to the effective channel 62 by translating and resizing the effective channel between at least a first lateral position and size (e.g., FIG. 5A) and a second lateral position and size (e.g., FIG. 5B), wherein the first and second lateral positions and sizes (i.e., with respect to a cross-sectional area) of the effective channel are different lateral positions perpendicular to the principal axis 58 of the orifice 36. It should be noted that the effective channel 62 is represented by a circle of various diameters extending via dashed lines in the sectional view of FIG. 5 for illustration purposes only; however, the effective channel can include other geometries.

In one embodiment, the control electronics 26 of FIG. 1 is configured to control the dynamic nozzle actuator 64 of FIG. 5 such that one or more actuators $64_3$ of responsive material are translated in an oscillating manner for partially blocking the orifice 36 in a controlled manner. For example, two actuators $64_3$ are shown (i) in FIG. 5A in a first lateral position that produces a first size of the effective channel 62, (ii) in FIG. 5B in a second lateral position that produces a second size of the effective channel 62, (iii) in FIG. 5C in a third lateral position that produces a third size of the effective channel 62 (similar in size to the first size), the third lateral position being similar to the first lateral position but on an opposite side of the principal axis 58, (iv) in FIG. 5D in a fourth lateral position that produces a fourth size of the effective channel 62 (similar in size to the second size), the fourth lateral position being similar to the second lateral position but on an opposite side of the principal axis 58, and (v) in FIG. 5E back to the first lateral position that produces the first size of the effective channel 62. Other suitable control of the dynamic nozzle actuator activation or activations for a given oral irrigator implementation are also possible.

Figure 7:
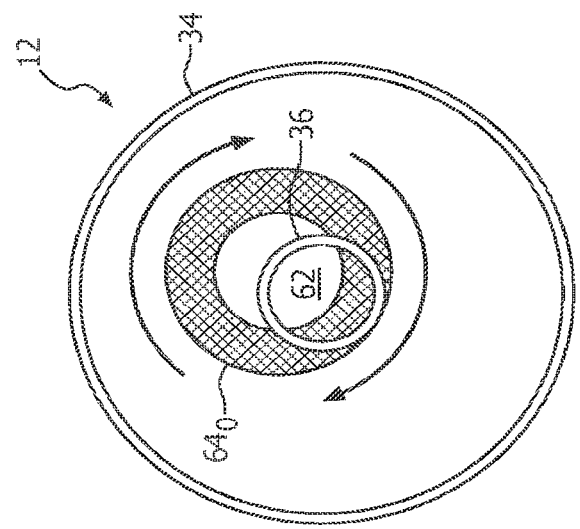
FIG. 7 is a top view of the nozzle design, similar to that of FIG. 5, including a dynamic nozzle actuator 64 for imparting a motion to an O-ring of responsive material translated in an oscillating manner for partially blocking an orifice 36 according to an embodiment of the present disclosure.
Figure 6:
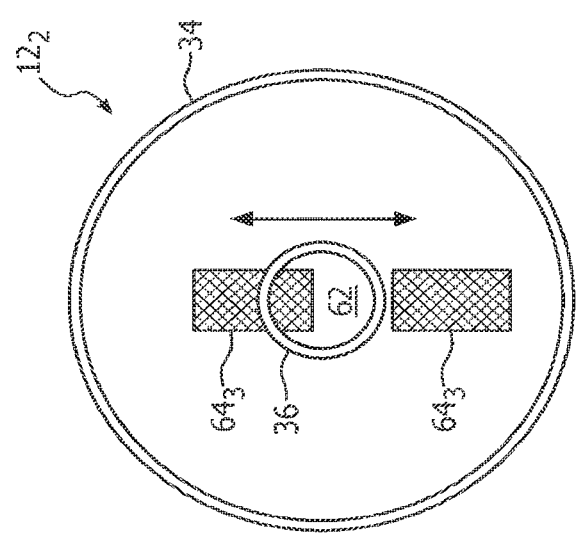
FIG. 6 is a top view of the nozzle design of FIG. 5 including the dynamic nozzle actuator for imparting a motion to one or more actuators translated in an oscillating manner for partially blocking an orifice 36 according to an embodiment of the present disclosure.

FIG. 6 illustrates a top view of the nozzle $12_2$ of FIG. 5 including the dynamic nozzle actuator 64 of responsive material for imparting a motion to one or more actuators $64_3$ translated in an oscillating manner for partially blocking the orifice 36 according to an embodiment of the present disclosure. In another embodiment, FIG. 7 illustrates a top view of the nozzle 12, similar to that of FIG. 5, including a dynamic nozzle actuator 64 for imparting a motion to an O-ring $64_O$ of responsive material translated in an oscillating manner for partially blocking the orifice 36. The oscillating manner for partially blocking the orifice 36 imparts motion to the effective channel 62 which can include one or more of a translation, rotation, resizing, and any combination thereof.

With reference to the embodiments of FIGS. 5, 6 and 7, a fluid spray angle is advantageously directed by adjusting (i.e., partially blocking) the effective channel 62 and fluid flow just before the orifice 36. The embodiment can be achieved by use of responsive materials that can be triggered to partially obstruct the fluid spray outlet (e.g., in an oscillatory manner) via actuating linearly oscillating 'actuators' or an eccentrically rotating o-ring. The partial obstruction advantageously adjusts the effective channel 62 and deflects the flow (i.e., spray) to increase a spray field coverage 56 (see FIGS. 5A and 5D). This can also be achieved via responsive materials that would change shape in such a fashion as to adjust the spray outlet in such a manner as described.

Turning now to FIG. 8 (8A, 8B, 8C), a sectional view of a nozzle 12 of the present invention including a dynamic nozzle actuator 64 for translating an effective channel 62 between at least two different sizes in by symmetrically narrowing or enlarging of the effective channel 62 according to an embodiment of the present disclosure is shown. In particular, for the embodiment of FIG. 8, the narrowing or enlarging of the effective channel is substantially symmetrical about the principal axis 58 through the orifice 36. In one embodiment, the control electronics 26 of FIG. 1 is configured to control the dynamic nozzle actuator 64 of FIG. 8 to impart a motion to the effective channel by resizing the effective channel between at least a first shape and a second shape, wherein the first shape and the second shape comprise at least two apertures of different cross-sectional shape. In another embodiment, the dynamic nozzle actuator resizes the effective channel between the first shape and the second shape in an iterative manner for consecutive bursts of expelled fluid. One or more actuators $64_4$ of responsive material are modulated, via control electronics in an oscillating manner for partially blocking the orifice 36. For example, two actuators $64_4$ are shown (i) in FIG. 8A in a first spaced apart position that produces a first aperture size of the effective channel 62, (ii) in FIG. 8B in a second spaced apart position that produces a second aperture size of the effective channel 62 (smaller in size to the first aperture size), and (iii) in FIG. 8C in a third spaced apart position that produces a third aperture size of the effective channel 62 (smaller in size to the second aperture size). Other suitable control of the dynamic nozzle actuator activation or activations for a given oral irrigator implementation are also possible.

With respect to the embodiment of FIG. 8, by changing a width of the fluid flow, the spray coverage 56 may be advantageously influenced, e.g., to cover (i) a wider area (FIG. 8A) with an initial powerful burst and (ii) a narrower area (FIGS. 8B and 8C) with secondary bursts within a single shot of fluid. For example, this can be achieved with the use of a dynamic nozzle actuator 64 made of responsive material that can change, upon appropriate energizing, of its inside diameter within a single shot of the device. Alternatively, this can be achieved in an iterative manner for consecutive bursts of expelled fluid.

Referring now to FIG. 9 (9A, 9B), there is shown a sectional view of a nozzle design of an oral irrigator device including a dynamic nozzle actuator 64 for imparting a motion to an effective channel between at least a first axial position (FIG. 9A) and a second axial position (FIG. 9B), different from the first axial position, according to an embodiment of the present disclosure. In one embodiment, the outer surface 60 of the guidance tip 34 operates as a spacer/alignment surface with respect to guidance tip 34. The contact point of the outer surface 60 between the teeth and the nozzle head advantageously provides support throughout multiple fluid shot(s) while the effective channel is retracting between the first and second axial positions. In one embodiment, the control electronics 26 are configured to control the dynamic nozzle actuator 64 (i) with both actuators $64_5$ and $64_6$ OFF as shown in FIG. 9A, (ii) with the both actuators $64_5$ and $64_6$ ON as shown in FIG. 9B, and (iii) any other suitable control of the dynamic nozzle actuator activation or activations for a given oral irrigator implementation. In one embodiment, an energizing of an actuator to an ON state results in a contraction of the responsive material, whereby the dynamic nozzle actuator 64 imparts a motion to the effective channel 62 translating the effective channel 62 between at least a first axial position (FIG. 9A) and a second axial position (FIG. 9B), wherein the first and second axial positions of the effective channel are different axial positions parallel to a principal axis 58 of the orifice 36. In addition, energizing of the actuator from the ON state to an OFF state results in an expansion of the responsive material to its non-energized condition or state, whereby the dynamic nozzle actuator 64 imparts a motion to the effective channel by translating the effective channel between at least the second axial position (FIG. 9B) and the first axial position (FIG. 9A). In another embodiment, the opposite may apply, wherein an ON state results in expansion of the responsive material and the OFF state results in a contraction of the responsive material. As a result, coverage of fluid spray is advantageously changed to have an interproximal reach that targets both approximal plaque and interproximal surface plaque, generally indicated by reference numerals 50 and 52, respectively, of neighbouring teeth 54 and 55, by retracting the effective channel or nozzle opening throughout a single shot or between consecutive shots of exhausted fluid. In a further embodiment, the dynamic nozzle actuator 64 translates the effective channel 62 between the first axial position (FIG. 9A) and the second axial position (FIG. 9B) in an iterative manner for consecutive bursts of expelled fluid.

Still further, with respect to the embodiment of FIG. 9, the tip of the structure implementing the effective channel 62 can be translated between (i) an initial registration position (similar to that shown in FIG. 9B) and (ii) a spray application position (similar to that shown in FIG. 9A), wherein the two positions are different axial positions along the principal axis 58. The initial registration position is used to initially register the effective channel's location properly, and then when the activation button is pushed to initiate a single shot or consecutive shots of exhausted fluid, the structure implementing the effective channel 62 is withdrawn to the spray application position for the shot or consecutive shots of exhausted fluid. In other words, the nozzle opening implemented via the effective channel 62 may be retracted, i.e., away from the tooth or teeth (i.e., 54 and 55), just before a shot of microburst fluid. In this manner, the structure implementing the effective channel 62 acts to guide the tip of the nozzle to locate the nozzle correctly between two teeth (similar to that shown in FIG. 9B) prior to the spray application, and a subsequent retraction of the structure implementing the effective channel 62 will spray the then visible tooth area (i.e., within the spray angle range of the effective aperture). In a further embodiment, the outer diameter of the nozzle head would continue to act as support of the head against the teeth such that nozzle location is maintained throughout single or multiple shots of the spray. In a further embodiment, the nozzle could be designed such that the nozzle opening retracts during the shot to access both the interdental and the visible areas of the teeth. In addition, passive materials could also be included with the use of the responsive materials, the passive materials using the momentum of the spray to induce the retraction, etc. These embodiments may further be extended to include any of the above embodiments for modulating the spray width or direction to further increase the spray coverage, effectively combining retraction and spray direction for maximum coverage.

With reference now to FIG. 10 (10A, 10B, 10C), a sectional view of a nozzle design of an oral irrigator device including a dynamic nozzle actuator for imparting a motion to an effective channel by rotating the effective channel between at least a first radial position (FIG. 10A) and a second radial position (FIG. 10B or FIG. 10C) according to an embodiment of the present disclosure is shown. The embodiment of FIG. 10 is similar to that of FIG. 9 with the following differences. The embodiment of FIG. 10 advantageously provides slight rotations of the nozzle head to direct the spray to cover a more directed area. The slight rotations are realized by using actuators $64_{10}$ made from responsive materials that can deform sufficiently under the influence of an electrical or optical signal or signals to coincide with the timing of either a single shot or multiple shots of exhausted fluid from the device. In another embodiment, only the nozzle tip or a smaller fraction of the center of the nozzle head with the nozzle tip is rotated, rather than rotating the whole nozzle head. In either case, a similar wide coverage angle effect can be achieved.

The contact point of the outer surface 60 between the teeth and the nozzle head advantageously provides support throughout multiple fluid shot(s) while the effective channel is retracting between the first and second radial positions. In one embodiment, the control electronics are configured to control the dynamic nozzle actuator 64 (i) with both actuators $64_5$ and $64_6$ OFF as shown in FIG. 10A, (ii) with the first actuator $64_5$ OFF and the second actuator $64_6$ ON as shown in FIG. 10B, (iii) with the first actuator $64_5$ ON and the second actuator $64_6$ OFF as shown in FIG. 10C, and (iv) any other suitable control of the dynamic nozzle actuator activation or activations for a given oral irrigator implementation. In one embodiment, an energizing of an actuator to an ON state results in a contraction of the responsive material, whereby the dynamic nozzle actuator imparts a motion to the effective channel by rotating the effective channel between at least a first radial position (e.g., FIG. 10A) and a second axial position (e.g., FIG. 10B or 10C), wherein the first and second radial positions of the effective channel are different radial positions with respect to the principal axis 58 of the orifice 36. In addition, energizing of the actuator from the ON state to an OFF state results in an expansion of the responsive material to its non-energized condition or state, whereby the dynamic nozzle actuator imparts a motion to the effective channel by rotating the effective channel between at least the second radial position (FIG. 10B or 10C) and the first radial position (FIG. 10A). In another embodiment, the opposite may apply, wherein an ON state results in expansion of the responsive material and the OFF state results in a contraction of the responsive material. As a result, coverage of fluid spray is advantageously changed to have an interproximal reach that targets both approximal plaque and interproximal surface plaque, generally indicated by reference numerals 50 and 52, respectively, of neighbouring teeth 54 and 55, by rotating the nozzle opening throughout a single shot or between consecutive shots of exhausted fluid. In a further embodiment, the dynamic nozzle actuator 64 rotates the effective channel 62 between the first radial position (FIG. 10A) and the second radial position (FIG. 10B or 10C) in an iterative manner for consecutive bursts of expelled fluid. In addition, the embodiment of FIG. 10 can be configured to achieve coverage from −15 degrees (FIG. 10B) to +15 degrees (FIG. 10C), where 0 degrees (FIG. 10A) represents the principal axis 58 aimed straight through the interproximal space between teeth 54 and 55. In a further embodiment, the actuators $64_5$, $64_6$ of responsive material each comprise a spring-like actuator configured to tilt an outer surface of the guidance tip in an oscillating manner.

Further with respect to the embodiment of FIG. 10, responsive to the at least one dynamic actuation of the effective channel, the at least one of (i) a direction of fluid expelled from the orifice, (ii) an angle of fluid expelled from the orifice, (iii) a cross-sectional width of fluid expelled from the orifice, and (iv) any combination thereof is dynamically influenced through a dynamic spray angle of, plus or minus, fifteen to thirty degrees (+/−15° to 30°) from a principal axis of the orifice.

FIG. 11 (11A, 11B, 11C) is a top view of a nozzle 12 of an oral irrigator device including a dynamic nozzle actuator $64_{11}$ for imparting a motion to an effective channel 62 by resizing a cross-sectional shape of the effective channel between at least a first shape (FIG. 11B) and a second shape (FIG. 11A or FIG. 11C) according to an embodiment of the present disclosure. In one embodiment, the dynamic nozzle actuator $64_{11}$, which comprises a portion of the orifice or channel as will be described further herein with reference to FIGS. 13-15, imparts a motion to the effective channel 62 or channel by resizing the effective channel between at least the first shape and the second shape, wherein the first shape and the second shape comprise at least two apertures of different cross-sectional shape. For example, the dynamic nozzle actuator can be configured to squeeze a diameter of the orifice between a lateral (or vertically oriented) oval, a circle, and a longitudinal (or horizontally oriented) oval. In addition, the effective channel 62 or may be changed throughout a single shot or between successive shots to increase the target area for more effective cleaning. That is, the dynamic nozzle actuator comprises one or more segments of responsive material that is configured to resize the effective channel between the first shape and the second shape in an iterative manner for consecutive bursts of expelled fluid. Furthermore, the embodiment of FIG. 11 advantageously influences direction and/or width of spray by changing the shape or direction of the effective channel of the nozzle tip from which the spray exits.

FIG. 12 (12A, 12B, 12C, 12D) is a top view of a nozzle 12 of an oral irrigator device including a dynamic nozzle actuator 64 for dynamically altering one or more actuator segments 64 of a cross-sectional shape of an effective channel 62 between at least two different altered cross-sectional shapes according to an embodiment of the present disclosure. For example, a first cross-sectional shape is shown in FIG. 12A, a second cross-sectional shape is shown in FIG. 12B, a third cross-sectional shape is shown in FIG. 12C and a fourth cross-sectional shape is shown in FIG. 12D. Other cross-sectional shapes are also possible. The dynamic nozzle actuator segments $64_{12}$ each comprise responsive material which changes shape when energized between ON and OFF states. The altered cross-sectional shapes advantageously influence direction and/or width of spray by locally changing the inner diameter of the effective channel 62. Accordingly, creating an effective channel 62 by partially obstructing the nozzle orifice 36 in an alternating pattern, the spray may be redirected within a single shot, to increase spray coverage. As with the embodiment of FIG. 5, this may be done by either having responsive materials actuate a moving obstruction or by having a responsive nozzle opening that is able to dynamically deform its shape, as described herein.

FIG. 13 (13A, 13B) is a sectional view of a nozzle 12 of an oral irrigator device including a dynamic nozzle actuator 64 for dynamically altering one or more dynamic nozzle actuator segments $64_9$ to create an effective channel 62 having a radius of curvature that is varied between at least two different radii ($R_1$ and $R_2$, wherein $R_1 > R_2$) according to another embodiment of the present disclosure. The dynamic nozzle actuator segments $64_9$ of FIG. 13 changes the effective channel 62 by resizing and/or reshaping a radius of curvature in a wall of the orifice 36 between at least the first radius of curvature and the second radius of curvature, wherein the first radius of curvature and the second radius of curvature establish at least two orifices having different rounded funnel shapes. In this embodiment, by changing a rounding of the nozzle outlet by means of the responsive materials, the spray angle 56 can be advantageously influenced to cover a wider area with an initial powerful burst and narrower area with secondary bursts within a single shot or between successive shots in a multiple shot mode of a microburst fluid. An increased coverage of spray is thus advantageously achieved.

FIG. 14 (14A, 14B) is a sectional view of a nozzle 12 of an oral irrigator device including a dynamic nozzle actuator 64 for dynamically altering one or more portions of the dynamic nozzle actuator 64 to effect a change in one or both radius of a nozzle bend in an effective channel 62 according to another embodiment of the present disclosure. In this embodiment, an increased coverage or angle of spray is achieved by changing one or both radius in the bend of the channel 38 proximate the end of nozzle 12 with use of responsive materials. In FIG. 14A, an inner radius segment 70 and an outer radius segment 72 of the dynamic nozzle actuator are in a first state for providing a first spray angle coverage. In FIG. 14B, the inner radius segment 70 and the outer radius segment 72 of the dynamic nozzle actuator are in a second state for providing a second spray angle coverage. Similarly, the inner radius segment 70 could be in the first state while the outer radius segment 72 could be in the second state, or vice versa, for providing further increased spray angle coverage. Accordingly, by changing one or both radius in the nozzle 12 bend by means of the responsive materials, the spray angle may be influenced, e.g., to cover a wider area with the initial powerful burst and narrower area with secondary bursts within a single shot of microburst fluid, or between successive shots in multiple shots mode of microburst fluid.

FIG. 15 (15A, 15B) is a sectional view of a nozzle 12 of an oral irrigator device including a dynamic nozzle actuator 64 for dynamically altering one or more cross-sectional shape of an orifice 36 between at least two different altered cross-sectional shapes according to another embodiment of the present disclosure. Similar to the embodiment of FIG. 13, the dynamic nozzle actuator 64 of FIG. 15 comprises one or more portions of a wall of the orifice 36 or channel 38, and imparts a motion to resize and/or reshape a perimeter of the orifice 36 between at least a first cross-sectional shape and the second cross-sectional shape, wherein the first shape and the second shape establish at least two orifices having different cross-sectional shapes. In this embodiment, by changing the cross-sectional shape of the orifice 36 from which the spray exits such that spray angle is influenced, an increased coverage of spray is advantageously achieved.

FIG. 16 (16A, 16B, 16C, 16D) is a top view and a sectional view of a nozzle 12 of an oral irrigator device including a plurality of orifices ($36_1$, $36_2$, $36_3$) or channels and a dynamic nozzle actuator 64 (FIG. 17) for dynamically influencing fluid expelled from the plurality of orifices 36 and for multiplexing the fluid expelled from the plurality of orifices 36 according to an embodiment of the present disclosure. In the embodiment of FIG. 16, the guidance tip 34 includes a plurality of orifices ($36_1$, $36_2$, $36_3$). In one embodiment, the plurality of orifices is used in an iterative manner for consecutive bursts of expelled fluid. For example, FIG. 16(A) illustrates use of orifice $36_1$ during a first shot of fluid spray to produce spray coverage $56_1$ at a first spray angle and width. FIG. 16(B) illustrates use of orifice $36_2$ during a second shot of fluid spray to produce spray coverage $56_2$ at a second spray angle and width. FIG. 16(C) illustrates use of orifice $36_3$ during a third shot of fluid spray to produce spray coverage $56_3$ at a third spray angle and width. FIG. 16(D) illustrates the plurality of orifices and the respective spray coverage obtained from each orifice. The dynamic nozzle actuator 64 as shown in FIG. 7 is configured to dynamically (a) influence at least one of (i) a direction of fluid, (ii) an angle of fluid, (iii) a cross-sectional width of fluid, and (iv) any combination thereof, expelled from the plurality of orifices ($36_1$, $36_2$, $36_3$) or channels and (b) multiplex the fluid expelled from among the plurality of orifices ($36_1$, $36_2$, $36_3$) or channels. FIG. 17 is a sectional view of a valve 74 configured for use with each of the plurality of orifices 36 of the multichannel nozzle 12 of FIG. 16 according to an embodiment of the present disclosure. While only one valve is shown, a plurality of valves is provided to correspond with the plurality of orifices 36. In this embodiment, the dynamic nozzle actuator 64 is coupled to the valve 74 for actuating the valve 74 between a closed state (FIG. 17A) and an open state (FIG. 17B). When the valve 74 is in its open state, an effective channel 62 is provided to correspond with the related orifice. In addition, one or more channels can be provided for the plurality of orifices.

Accordingly, in one embodiment, two (or more) effective channels of nozzle outlets are combined with one or more parts made of responsive material or activated by responsive material to switch a fluid flow between the plurality of effective channels in the nozzle head within a single shot of microburst fluid, or between successive shots of microburst fluid in a multiple shots mode. The effective channels are positioned at different angles, thus providing greater microburst spray coverage during treatment.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in other healthcare applications, such as water jets or other applications that use a spray-based principle requiring a nozzle. In addition, actuation of the responsive material may also include other types of actuation, for example, pH change, light guides, etc. Furthermore, combinations of any of the above-mentioned embodiments or comparable solutions that would yield a more effective coverage and subsequent cleaning via (geometric) changes of the nozzle shape, fluid path and/or spray direction are contemplated. Moreover, with respect to the embodiments, care is taken that modulating spray direction, width or other characteristics are realized such that effective spray dynamics (e.g. loss of energy or of droplet speed or change in droplet size distribution) are not adversely affected such that the resulting spray would no longer be effective. Some embodiments may be designed to enhance the spray dynamics. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A nozzle for an oral irrigator device, comprising:
an elongated body having a channel;
a guidance tip located at one end of the elongated body, wherein said guidance tip includes an orifice coupled to the channel and configured to expel a fluid as one of a jet, a spray, or any combination thereof; and
a dynamic nozzle actuator positioned within said guidance tip, wherein said dynamic nozzle actuator comprises at least one responsive material adapted for being energized in a prescribed manner and configured to implement at least one dynamic actuation of an effective channel for dynamically influencing at least one of (i) a direction of fluid expelled from the orifice, (ii) a spray angle of fluid expelled from the orifice, and (iii) a cross-sectional width of fluid expelled from the orifice, wherein the at least one dynamic actuation of the effective channel comprises a motion imparted to the effective channel selected from the group consisting of translation, rotation, and resizing, and further wherein said dynamic nozzle actuator is configured to impart a motion to the effective channel by at least one selected from the group consisting of (A) translating the effective channel between a first position and a second position, wherein the first and second positions of the effective channel are different lateral positions perpendicular to a principal axis of the orifice, and (B) rotating the effective channel between at least a first radial position and a second radial position with respect to a plane perpendicular to the principal axis of the orifice.

2. The nozzle of claim 1, wherein the at least one responsive material comprises one or more of (i) an electroactive polymer (EAP), (ii) a shape memory alloy (SMA), (iii) a bimetal, and (iv) a piezo (PZT) material.

3. The nozzle of claim 1, further wherein said dynamic nozzle actuator is configured to impart the motion to the effective channel by translating the effective channel between the first position and the second position, in an iterative manner for consecutive bursts of expelled fluid.

4. The nozzle of claim 1, wherein the responsive material further comprises one selected from the group consisting of (i) one or more actuators of responsive material configured to be translated in an oscillating manner to partially block the orifice and (ii) an o-ring of responsive material configured to be translated in an oscillating eccentric manner to partially block the orifice.

5. The nozzle of claim 1, wherein responsive to the at least one dynamic actuation of the effective channel, the at least one of (i) a direction of fluid expelled from the orifice, (ii) a spray angle of fluid expelled from the orifice, and (iii) a cross-sectional width of fluid expelled from the orifice is configured to be dynamically influenced through a dynamic spray angle of, plus or minus, fifteen to thirty degrees (+/−15° to) 30°) from the principal axis of the orifice.

6. The nozzle of claim 5, wherein said dynamic nozzle actuator is configured to impart the motion to the effective channel and rotate rotating the effective channel between at least the first radial position and the second radial position.

7. The nozzle of claim 6, further wherein said dynamic nozzle actuator is configured to rotate the effective channel between the first radial position and the second radial position in an iterative manner for consecutive bursts of expelled fluid.

8. The nozzle of claim 7, further wherein the orifice comprises the effective channel and is located in an outer surface of said guidance tip, and wherein the responsive material further comprises a spring-like actuator configured to tilt the outer surface of said guidance tip in an oscillating manner.

9. The nozzle of claim 1, further wherein said dynamic nozzle actuator is configured to impart a further motion to the effective channel which resizes the effective channel between at least a first shape and a second shape, wherein the first shape and the second shape comprise at least two apertures of different cross-sectional shape.

10. The nozzle of claim 9, further wherein the effective channel comprises a given cross-sectional shape and wherein said dynamic nozzle actuator is further configured to control the at least one responsive material and dynamically alter the cross-sectional shape of the effective channel between at least two different altered cross-sectional shapes.

11. The nozzle of claim 1, wherein said guidance tip further includes a plurality of orifices, and wherein said dynamic nozzle actuator is configured to dynamically (a) influence at least one of (i) a direction of fluid, (ii) a spray angle of fluid, and (iii) a cross-sectional width of fluid expelled from the plurality of orifices and (b) multiplex the fluid expelled from among the plurality of orifices.

\* \* \* \* \*